United States Patent

Mori et al.

Patent Number: 5,237,102
Date of Patent: Aug. 17, 1993

[54] SULFONE ALDEHYDES USEFUL FOR PRODUCING β-CAROTENE

[75] Inventors: Toshiki Mori; Hiroshi Fujii; Takashi Onishi, all of Kurashiki; Kazuo Yamamoto, Niigata, all of Japan

[73] Assignee: Kuraray Company Ltd., Kurashiki, Japan

[21] Appl. No.: 937,375

[22] Filed: Aug. 31, 1992

Related U.S. Application Data

[62] Division of Ser. No. 706,209, May 28, 1991, Pat. No. 5,185,468.

[30] Foreign Application Priority Data

Jun. 14, 1990 [JP] Japan .................. 2-156869
Jun. 14, 1990 [JP] Japan .................. 2-156870
Sep. 25, 1990 [JP] Japan .................. 2-256028

[51] Int. Cl.$^5$ .......................... C07C 317/10
[52] U.S. Cl. ................................. 568/31
[58] Field of Search ......................... 568/31

[56] References Cited

U.S. PATENT DOCUMENTS 4,331,814  5/1982  Chabaras et al.
4,474,983  10/1984  Chabaras et al.
4,883,887  11/1989  Bernhard et al. ............. 568/31

*Primary Examiner*—Marianne M. Cintins
*Assistant Examiner*—John Peabody
*Attorney, Agent, or Firm*—Oblon, Spivak, McClelland, Maier & Neustadt

[57] ABSTRACT

Provided is a novel process for readily producing β-carotene in which a sulfone compound represented by the general formula (1), (2) or (3) is reacted with an alkali,

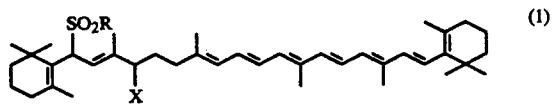

(1)

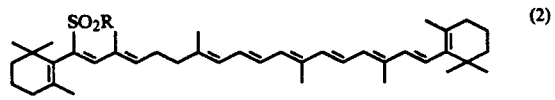

(2)

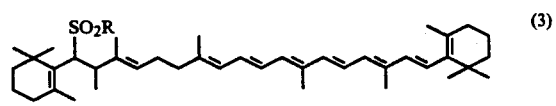

(3)

wherein R represents a phenyl group which may be substituted, R' a protecting group of acetal type and X a halogen atom.

10 Claims, No Drawings

SULFONE ALDEHYDES USEFUL FOR PRODUCING β-CAROTENE

This is a division of application Ser. No. 07/706,209, filed on May 28, 1991, now U.S. Pat. No. 5,185,468.

BACKGROUND OF THE INVENTION

1. Field of the Invention

The present invention relates to a process for producing beta(β)-carotene and novel intermediate compounds useful for the process.

β-carotene is a valuable compound used as a food additive and the like.

2. Description of the Related Art

It is known that β-carotene is synthesized for example by the following processes.

(A) A process comprising reacting by way of acetylenediol. See Helv. Chim. Acta., 39 (27), 249 (1956).

(B) A process comprising reacting vitamin A phosphonium salt with hydrogen peroxide. See Japanese Patent Publication No. 10659/1984.

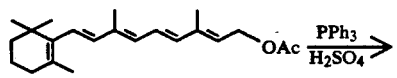
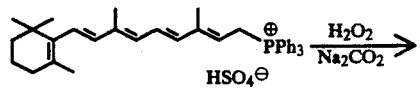
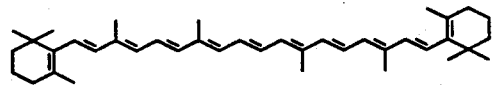

(C) A process comprising synthesizing from vitamin A phosphonium salt and vitamin A aldehyde. See German Patent 1,068,709 (1958).

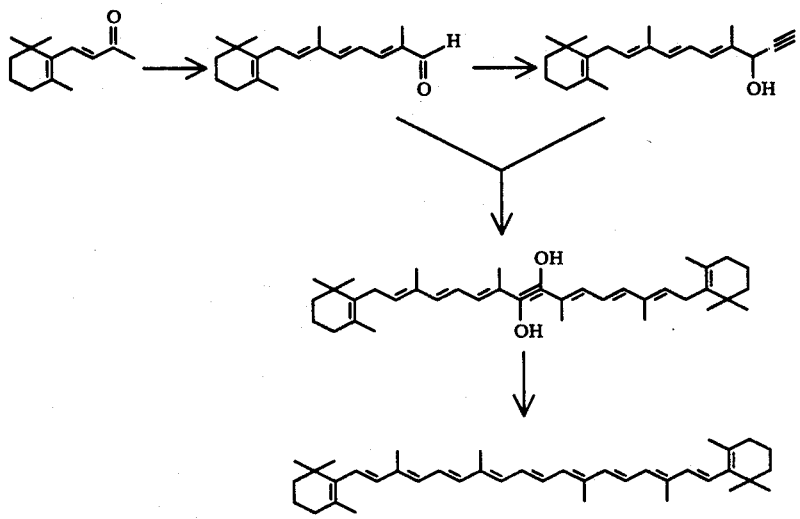

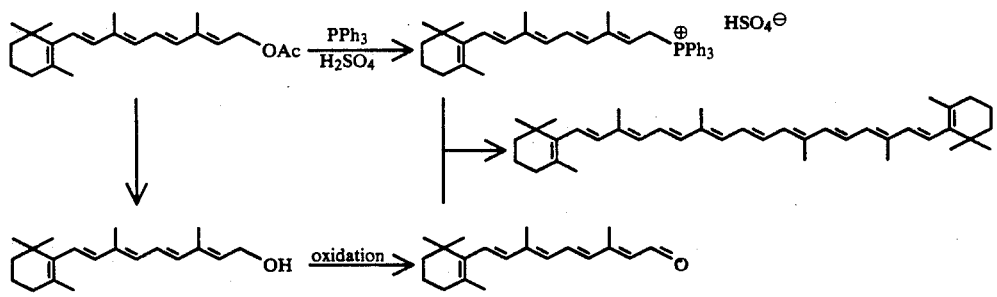

(D) A process comprising synthesizing from vitamin A sulfone and vitamin A halide. See Japanese Patent Application Laid-open No. 5543/1973.

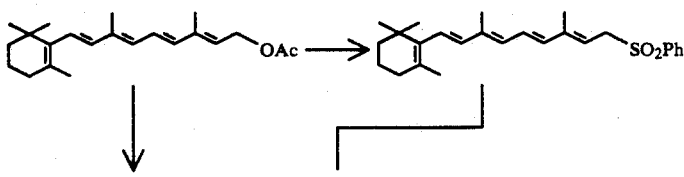

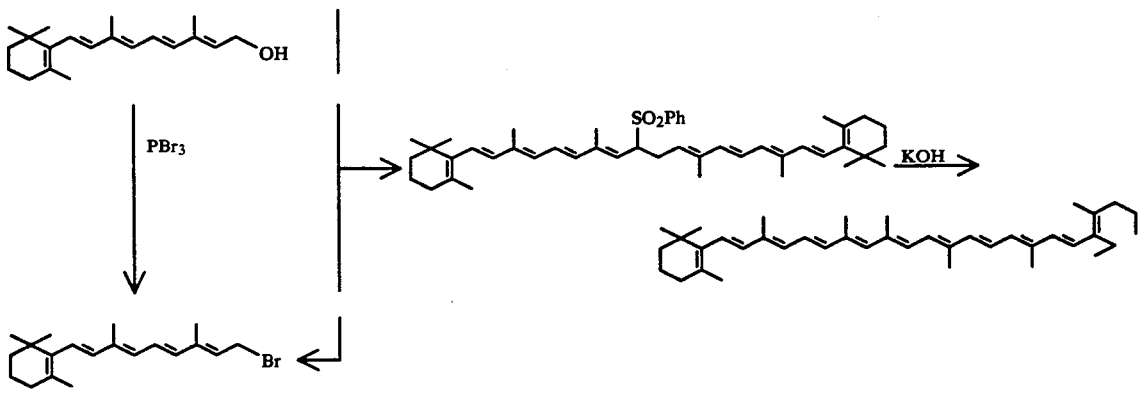

The above syntheses for β-carotene have the following drawbacks.

Process (A) synthesizes β-carotene from the starting compound β-ionone while requiring so many reaction stages;

Process (B) requires triphenyl phosphine in an equivalent amount based on the mole of vitamin A and must use a hazardous peroxide;

Process (C) must separately synthesize vitamin A aldehyde from vitamin A which is unstable when exposed to heat or acid; and Process (D) must separately synthesize vitamin A halide which is extremely unstable when heated.

Accordingly an object of the present invention is to provided an improved process for producing β-carotene easily and from starting materials that are inexpensive and readily available.

Another object of the present invention is to provide a novel intermediate product used advantageously for the above improved process.

Other objects and advantages of the present invention will become apparent from the following descriptions.

SUMMARY OF THE INVENTION

The present invention provides a process for producing β-carotene which comprises reacting a sulfone compound represented by the general formula (1), (2) or (3) with an alkali,

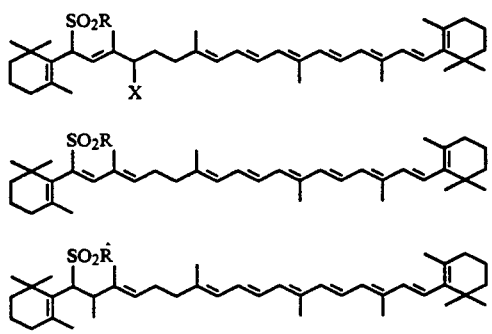

wherein R represents a phenyl group which may be substituted, R' a protecting group of acetal type and X a halogen atom; and also a process for producing β-carotene which comprises oxidizing a sulfone alcohol represented by the general formula (4), (5) or (6),

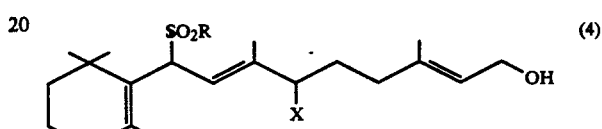

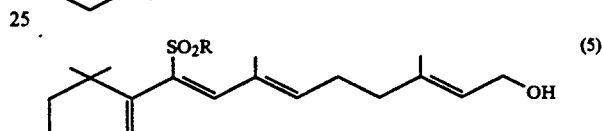

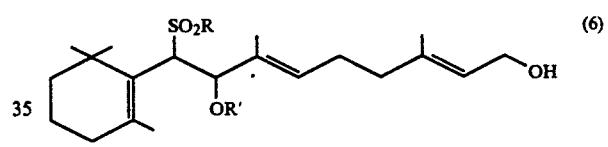

wherein R, R' and X are the same as defined above, to obtain a sulfone aldehyde represented by the following general formula (7), (8) or (9);

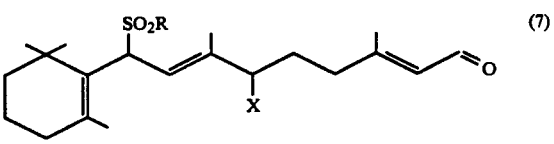

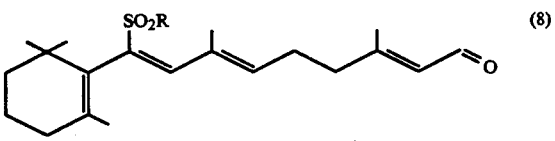

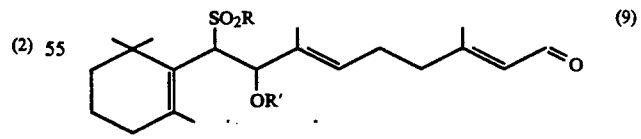

coupling the sulfone aldehyde with vitamin A phosphonium salt to obtain the afore-mentioned sulfone compound of the formula (1), (2) or (3); and reacting the obtained sulfone compound with an alkali.

DETAILED DESCRIPTION OF THE PREFERRED EMBODIMENTS

The sulfone alcohols represented by the formula (4), (5) and (6) and used as the starting material in the above process are known important intermediate products for synthesizing vitamin A. See for example U.S. Pat. Nos. 4,825,006 and 4,876,400 and Japanese Patent Application Laid-open Nos. 87559/1987, 89652/1987 and 59/1987. They disclose the following processes to obtain the intermediate products.

Oppenauer oxidation utilizing a tertiary aldehyde in the presence of an aluminum catalyst.

The oxidation processes used for this purpose are described more concretely below. The oxidation of sulfone alcohols represented by the formulas (4), (5) and (6) utilizing manganese dioxide comprises using 2 to 10

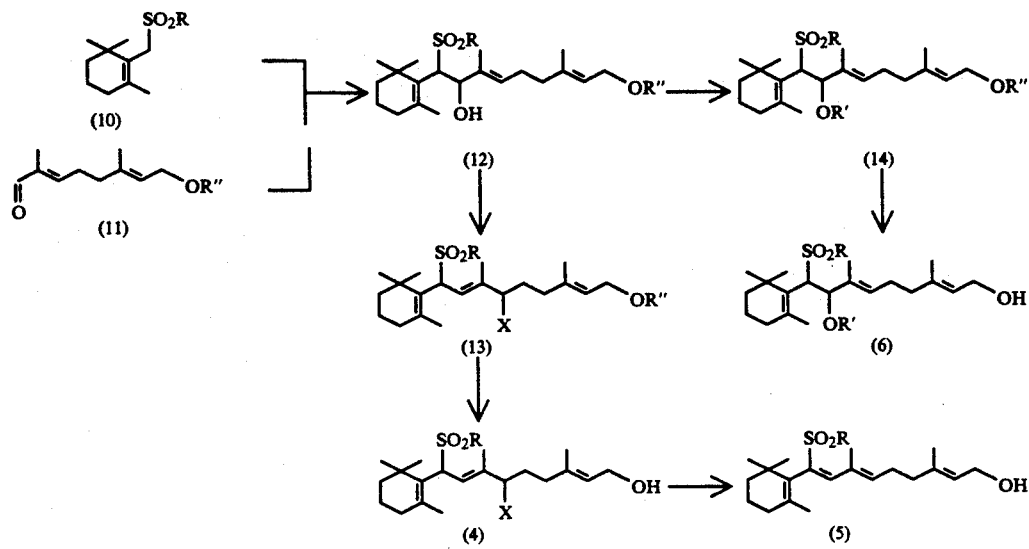

wherein R, R' and X are the same as defined before and R" represents a lower acyl group.

A hydroxysulfone represented by the general formula (12) can be obtained by coupling a β-cyclogeranylphenyl sulfone derived from linalol and represented by the general formula (10) with an aldehyde represented by the general formula (11) and derived from the carboxylate of geraniol under an alkaline condition. The hydroxysulfone is reacted with a halogenizing agent such as thionyl chloride or phosphorus tribromide to give a halosulfone ester represented by the general formula (13), which is then hydrolyzed by sodium hydroxide or the like to give a sulfone alcohol represented by the formula (4). The sulfone alcohol obtained gives, by reaction with sodium hydroxide or a tertiary amine, a sulfone alcohol represented by the formula (5). Besides, the hydroxysulfone represented by the formula (12) is acetalized to give a sulfone acetal represented by the formula (14), which is then hydrolyzed by sodium hydroxide or the like to give a sulfone alcohol represented by the formula (6).

The R, R' and X in the above formulas are now described in detail. R represents a phenyl group which may be substituted. Examples of the substituting group are lower alkyl groups such as methyl, ethyl, i-propyl, n-propyl, i-butyl and n-butyl; halogens such as chloride, bromide and iodide and lower alkoxy groups such as methoxy, ethoxy, i-propoxy, n-propoxy, i-butoxy and n-butoxy. The substituting group can be, alone or in plurality, present in any position of ortho, meta or para. R' represents a protecting group of acetal type and its examples are those having a carbon skeleton, e.g. 1-ethoxyethyltetrahydrofuranyl, tetrahydropyranyl and 4-methyltetrahydropyranyl. X represents a halogen atom, e.g. chlorine, bromide and iodine.

The sulfone alcohols obtained by the above processes can readily be converted into the corresponding sulfone aldehydes (7), (8) and (9) respectively, by a mild oxidation process, such as one utilizing manganese dioxide or times by weight of manganese dioxide based on the weight of the sulfone alcohol and a reaction solvent of a hydrocarbon solvent, e.g. benzene and toluene, a halohydrocarbon, e.g. methylene chloride, chloroform and 1,2-dichloroethane, an ether solvent, e.g. diethyl ether, diisopropyl ether and tetrahydrofuran or an ester solvent, e.g. ethyl acetate and butyl acetate. The reaction is preferably conducted at a temperature of 10° to 50° C., and is generally completed in 30 minutes to 10 hours. After completion of the oxidation, the insoluble manganese dioxide is removed by filtration and the solvent is removed, to obtain the sulfone aldehyde represented by the formula (7), (8) or (9).

The oxidation of the sulfone alcohols represented by the formulas (4), (5) and (6) utilizing a tertiary aldehyde in the presence of an aluminum catalyst comprises reacting the sulfone alcohols with 1.1 to 5 molar equivalent of a tertiary aldehyde in the presence of 2 to 10 mol % based on the mole of the sulfone alcohol of an aluminum catalyst. Examples of the aluminum catalyst are aluminum triisopropoxide, aluminum tri-tert-butoxide, aluminum tri-sec-butoxide and aluminum triphenoxide. Examples of the tertiary aldehyde are trimethylacetaldehyde, 2,2-dimethylbutanal, 2-ethyl-2-methylbutanal, 2,2-dimethyl-4-pentenal, 2,2-dimethylpentanal and 2,2-dimethylpenta-3,4-dienal. Examples of the solvent are hydrocarbon solvents, e.g. benzene and toluene, halohydrocarbon solvents, e.g. methylene chloride, chloroform and 1,2-dichloroethane, ether solvents, e.g. diethyl ether, diisopropyl ether and tetrahydrofuran and ester solvents, e.g. ethyl acetate and butyl acetate. The reaction is generally effected at a temperature of 10° to 60° C. and completed in 30 minutes to 6 hours. This reaction terminates by addition of water or an aqueous solution of hydrochloric acid, sulfuric acid, acetic acid or the like. After the termination of the reaction, the reaction mixture is subjected to extraction with the reaction solvent used, i.e. toluene, diethyl ether, methylene chloride, ethyl acetate or the like. The organic layer extracted is then separated and washed and the solvent is removed therefrom, to give the sulfone aldehyde represented by the corresponding formula (7), (8) or (9). Where the reaction has been terminated by addition of a small amount of water, low boiling compounds in the reaction mixture can be removed by distillation under a reduced pressure to obtain the sulfone aldehyde.

The sulfone aldehyde represented by the formula (7), (8) or (9) and obtained by the above oxidation process can be used as it is, or after being purified and isolated by column chromatography or like methods, for producing the corresponding sulfone compound represented by the formula (1), (2) or (3).

The sulfone aldehydes represented by the formulas (7), (8) and (9) are novel compounds not seen in the literature, and so are the sulfone compounds represented by the formulas (1), (2) and (3).

The sulfone compounds represented by the formula (1), (2) and (3) are produced by the following process. Vitamin A and vitamin A acetate are reacted with an at least equivalent amount of triphenylphosphine and sulfuric acid in an alcohol solvent, e.g. methanol and ethanol, at 0° to 50° C. for 30 minutes to 8 hours, to give vitamin A phosphonium salt. The solvent used can be replaced by another solvent, such as water or an amide solvent, e.g. N,N-dimethylformamide. To the vitamin A phosphonium salt thus obtained is added a solution of the sulfone aldehyde represented by the formula (7), (8) or (9) in an alcohol solvent, such as methanol or ethanol, a halohydrocarbon solvent such as methylene chloride, chloroform or carbon tetrachloride or an amide solvent such as N,N-dimethylformamide, and to the mixture an aqueous solution of an alkali such as potassium hydroxide or sodium hydroxide is gradually added dropwise in an amount of at least 1 equivalent at 0° to 60° C., to obtain the corresponding sulfone compound represented by the formula (1), (2) or (3). The crude product thus obtained is purified by extracting the product with an extracting solvent of a halohydrocarbon solvent such as methylene chloride or chloroform, a hydrocarbon solvent such as toluene or benzene, an ether solvent such as diethyl ether or diisopropyl ether or an ester solvent such as ethyl acetate or butyl acetate, separating the extract, and washing it with water an aqueous sodium carbonate solution or the like, followed by removal of the solvent by distillation. The sulfone compound thus obtained and represented by the formula (1), (2) or (3) can be used as it is for the next step of synthesizing β-carotene, or may, before the synthesis, be purified and isolated by column chromatography or the like.

The sulfone compounds represented by the formulas (1), (2) and (3) are reacted with an alkaline compound to give β-carotene. Examples of the alkaline compound are potassium alkoxide, e.g. potassium methoxide, potassium ethoxide and potassium t-butoxide, other alkali metal alkoxide, e.g. sodium methoxide, sodium ethoxide, sodium t-butoxide, lithium methoxide, lithium ethoxide and lithium t-butoxide, and alkali metal hydroxides, e.g. potassium hydroxide, sodium hydroxide and lithium hydroxide, among which potassium compounds can give β-carotene at a high yield. The above alkaline compounds are used in an amount of about 2 to 20 moles based on the mole of the sulfone compound represented by the formula (1), (2) or (3). The reaction solvent used is selected depending on the type of the alkaline compound used, i.e. a hydrocarbon solvent such as hexane, cyclohexane, benzene or toluene for the alkaline compound of an alkali metal alkoxide and an alcohol solvent such as methanol, ethanol or propanol for an alkali metal hydroxide. The reaction is generally effected at 10° to 120° C. After completion of the reaction, the reaction mixture is subjected to extraction with an organic extraction solvent of toluene, diethyl ether, methylene chloride or ethyl acetate and the organic extraction layer is washed with water, an aqueous sodium carbonate solution or the like, followed by removal of the solvent, to give the corresponding β-carotene.

The β-carotene thus obtained can be purified by direct recrystallization or column chromatography, or first subjected to heat refluxing for a few hours in a solvent of a non-polar solvent such as n-heptane or water and then to recrystallization or column chromatography, to give pure β-carotene.

Other features of the invention will become apparent in the course of the following descriptions of exemplary embodiments which are given for illustration of the invention and are not intended to be limiting thereof.

EXAMPLE 1

Synthesis of 6-chloro-3,7-dimethyl-9-(2,6,6-trimethyl-1-cyclohexen-1-yl)-9-phenylsulfonyl-2,7-nonadien-1-al with manganese dioxide

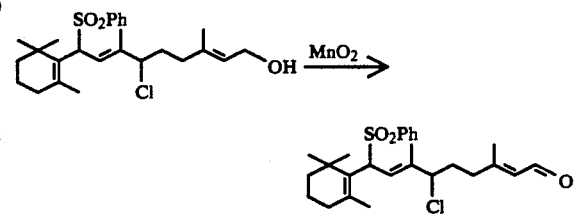

A 200-ml round-bottom flask was charged with a solution of 3.9 g (purity: 89.3%, 7.5 mmoles) of 6-chloro-1-hydroxy-3,7-dimethyl-9-(2,6,6-timethyl-1-cyclohexen-1-yl)-9-phenylsulfonyl-2,7-nonadiene in 50 ml of methylene chloride and then with 20 g of manganese dioxide, and the mixture was stirred at 25° C. for 3 hours. Then manganese dioxide remaining undissolved was removed by filtration and the solvent was distilled off in vacuo, to obtain 3.3 g of a crude oily substance. Purification of this substance by column chromatography (hexane/ethyl acetate=7/3) gave 3.1 g (6.7 mmoles, yield: 89.3%) of 6-chloro-3,7-dimethyl-9-(2,6,6-trimethyl-1-cyclohexen-1-yl)-9-phenylsulfonyl-2,7-nonadien-1-al. The chemical structure of the product thus obtained was confirmed by the following instrumental analyses data.

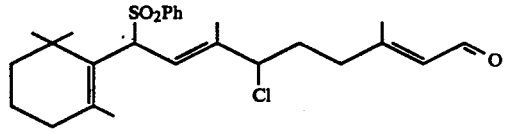

6-Chloro-3,7-dimethyl-9-(2,6,6-trimethyl-1-cyclohexen-1-yl)-9-phenylsulfonyl-2,7-nonadien-1-al NMR (CDCl$_3$) TMS δ: 0.8–2.1 (m, 25H), 4.3–4.65 (m, 2H), 5.8–6.1 (m, 2H), 7.5–8.0 (m, 5H), 9.9 (d, 1H).

IR Film ν (cm$^{-1}$): 1670 (C=O), 1140 (SO$_2$)

FD-MS m/e: 504 (M+), 505 (M+), 468 (M+—HCl).

EXAMPLE 2

Synthesis of 6-chloro-3,7-dimethyl-9-(2,6,6-trimethyl-1-cyclohexen-1-yl)-9-phenylsulfonyl-2,7-nonadien-1-al with aluminum triisopropoxide and trimethylacetaldehyde

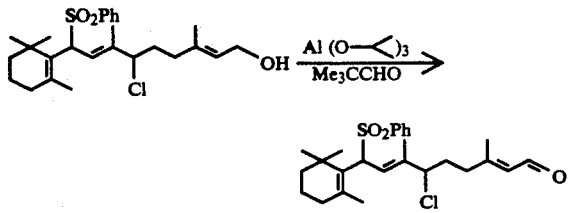

A 100-ml round-bottom flask was charged with a solution of 4.2 g (purity: 89.3%, 8.1 mmoles) of 6-chloro-1-hydroxy-3,7-dimethyl-9-(2,6,6-trimethyl-1-cyclohexen-1-yl)-9-phenylsulfonyl-2,7-nonadiene, 78 mg (0.36 mmole) of aluminum triisopropoxide and 21.1 g (24.3 mmoles) of trimethylacetaldehyde, and the mixture was stirred at 50° C. for 2 hours. Then the reaction was terminated by addition of 0.3 ml of water. The reaction mixture was distilled in vacuo to remove off low boiling fractions, to give 4.15 g (purity: 81.0%, 7.27 mmoles, yield: 90%) of a crude 6-chloro-3,7-dimethyl-9-(2,6,6-trimethyl-1-cyclohexen-1-yl)-9-phenylsulfonyl-2,7-nonadien-1-al.

Sulfone aldehydes were synthesized by (A) the oxidation using manganese dioxide and (B) that using aluminum triisopropoxide and trimethylacetaldehyde, in the same manner as in Examples 1 and 2 respectively. The results are shown in the Table below.

IR Tablet ν (cm$^{-1}$): 1675 (C=O), 1140 (SO$_2$).
FD-MS m/e: 426 (M+)

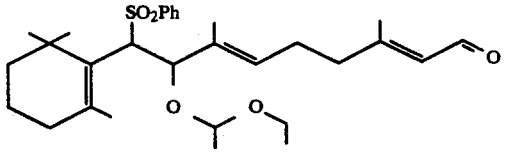

8-(1-Ethoxy)ethoxy-3,7-dimethyl-9-(2,6,6-trimethyl-1-cyclohexen-1-yl)-9-phenylsulfonyl-2,6-nonadien-1-al NMR (CDCl$_3$) TMS δ: 0.8–2.3 (m, 31H), 3.4–5.1 (m, 5H), 5.4 (m, 1H), 5.9 (d, 1H), 7.5–8.0 (m, 5H), 9.9 (d, 1H).
IR Film ν (cm$^{-1}$): 1670 (C=O), 1140 (SO$_2$).
FD-MS m/e: 516 (M+).

EXAMPLE 7

Synthesis of 1-phenylsulfonyl-4-chloro-1,18-di(2,6,6-trimethyl-1-cyclohexen-1-yl)-3,7,12,16-tetramethyloctadeca-2,7,9,11,13,15,17-heptaene from vitamin A phosphonium salt and 6-chloro-3,7-dimethyl-9-(2,6,6-trimethyl-1-cyclohexen-1-yl)-9-phenylsulfonyl-2,7-nonadien-1-al)

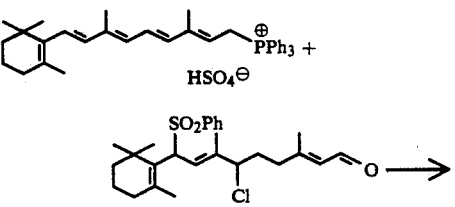

| Synthesis Examples of sulfone aldehydes | | | | |
|---|---|---|---|---|
| Sulfone alcohol | Sulfone aldehyde | Example | Oxidation | Yield (%) |
| ![](SO2Ph...OH) | ![](SO2Ph...O) | 3 | A | 85.0 |
|  |  | 4 | B | 89.0 |
| ![](SO2Ph...OH) | ![](SO2Ph...O) | 5 | A | 83.7 |
|  |  | 6 | B | 91.0 |

Notes:
A: oxidation with manganese dioxide
B: oxidation with aluminum triisopropoxide and trimethylacetaldehyde Instrumental analyses data of the sulfone aldehydes obtained

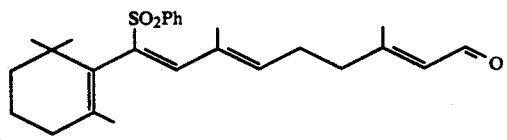

3,7-Dimethyl-9-(2,6,6-trimethyl-1-cyclohexen-1-yl)-9-phenylsulfonyl-2,6,8-nonatrien-1-al NMR (CDCl$_3$) TMS δ: 0.9–2.5 (m, 25H), 5.7–6.0 (m, 3H), 7.5–8.0 (m, 5H), 9.9 (d, 1H).

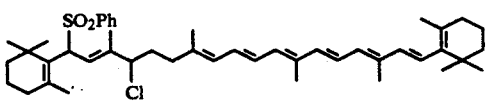

A 100-ml round-bottom flask was charged with a solution of 2.14 g (6.4 mmoles) of vitamin A acetate, 1.68 g (6.4 mmoles) of triphenylphosphine and 0.64 g (6.4 mmoles) of concentrated sulfuric acid in 10 g of methanol, and the contents were stirred at 25° C. for 3 hours. Thereafter, methanol was removed by distillation in vacuo from the reaction mixture to obtain a tar-like vitamin A phosphonium salt. This was dissolved in 10 g of water and to the solution was added 10 ml of a solution of 3.0 g (6.4 mmoles) of 6-chloro-3,7-dimethyl-9-(2,6,6-trimethyl-1-cyclohexen-1-yl)-9-phenylsulfonyl-2,7-nonadien-1-al in methylene chloride. To this mixture was added gradually 10.84 g (12.8 mmoles) of a 7.7% aqueous solution of potassium hydroxide at 8° C., and the resulting mixture was stirred for 30 minutes. After completion of the reaction, an organic layer was separated from an aqueous layer and washed with water, followed by distilling off of the solvent, to give 6.72 g (purity: 40.9%, 3.85 mmoles, yield: 60.2%) of an oily substance. This substance was purified by silica gel chromatography (hexane/ethyl acetate=85/15) to give 2.05 g of 1-phenylsulfonyl-4-chloro-1,18-di(2,6,6-trimethyl-1-cyclohexen-1-yl)-3,7,12,16-tetramethyloctadeca-2,7,9,11,13,15,17-heptaene.

The chemical structure of the product thus obtained was confirmed by the following instrumental analyses data.

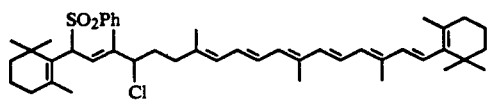

1-Phenylsulfonyl-4-chloro-1,18-di(2,6,6-trimethyl-1-cyclohexen-1-yl)-3,7,12,16-tetramethyloctadeca-2,7,9,11,13,15,17-heptaene NMR (CDCl$_3$) TMS δ: 0.8–2.2 (m, 46H), 4.3–4.6 (m, 2H), 5.8–6.7 (m, 10H), 7.5–8.0 (m, 5H).
IR Tablet ν (cm$^{-1}$): 1140 (SO$_2$), 2910 (C—H).

EXAMPLES 8 AND 9

Sulfone compounds were synthesized from the corresponding sulfone aldehydes and vitamin A phosphonium salt in the same manner as in Example 7. The results are shown in the Table below.

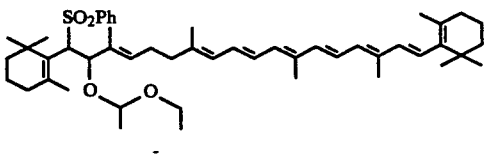

7-Phenylsulfonyl-8-(1-ethoxy)ethoxy-11,12-dihydro-β-carotene

NMR (CDCl$_3$) TMS δ: 0.8–2.3 (m, 52H), 3.4–5.1 (m, 5H), 5.8–6.8 (m, 10H), 7.5–8.0 (m, 5H).
IR Tablet ν (cm$^{-1}$): 1140 (SO$_2$), 2910 (C—H).

EXAMPLE 10

Synthesis of β-carotene from 1-phenylsulfonyl-4-chloro-1,18-di(2,6,6-trimethyl-1-cyclohexen-1-yl)-3,7,12,16-tetramethyloctadeca-2,7,9,11,13,15,17-heptaene with potassium methoxide

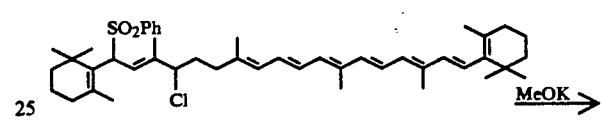

In a 50-ml round-bottom flask 2.01 g (purity: 40.9%, 1.15 mmoles) of 1-phenylsulfonyl-4-chloro-1,18-di(2,6,6-trimethyl-1-cyclohexen-1-yl)-3,7,12,16-tetramethyloctadeca-2,7,9,11,13,15,17-heptaene was reacted with 1.0 g (purity: 80%, 11 mmoles) of potassium methoxide in 4 g of toluene at 30° C. for 2 hours. Then water was added to the reaction mixture. The resulting or-

| | Synthesis Examples of sulfone compounds from vitamin A and sulfone aldehydes | |
|---|---|---|
| Example | Sulfone aldehyde | Sulfone compound | Yield (%) |
| 8 | 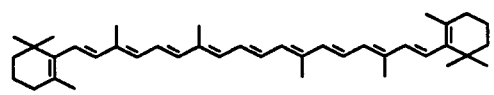 | | 65.0 |
| 9 | | | 66.0 |

Instrumental analyses data of the sulfone aldehydes obtained

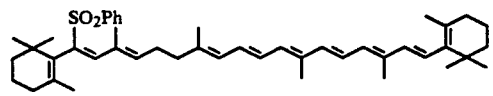

7-Phenylsulfonyl-11,12-dihydro-β-carotene

NMR (CDCl$_3$) TMS δ: 0.9–2.5 (m, 46H), 5.7–6.8 (m, 11H), 7.5–8.0 (m, 5H).
IR Tablet ν (cm$^{-1}$): 1140 (SO$_2$), 2910 (C—H).

ganic layer was separated and washed with water, followed by removal of the solvent, to give 2.58 g (purity: 19.1%, 0.918 mmole, yield: 80%) of a crude β-carotene. To this product 10 g of water was added. The mixture was heat-refluxed for 10 hours and subjected to extraction with toluene to remove organic substances, followed by recrystallization of the residue from toluene-methanol solvent, to give 44 mg of a dark brown crystal. The crystal thus obtained was confirmed to be β-carotene by comparison with standard sample.
m.p.: 177°–178° C.
λ max: 455 nm (E$_1$ $_{cm}$$^1$%=2.350, cyclohexane).

EXAMPLE 11

Synthesis of β-carotene from 1-phenylsulfonyl-4-chloro-1,18-di(2,6,6-trimethyl-1-cyclohexen-1-yl)-3,7,12,16-tetramethyloctadeca-2,7,9,11,13,15,17-heptaene with potassium hydroxide

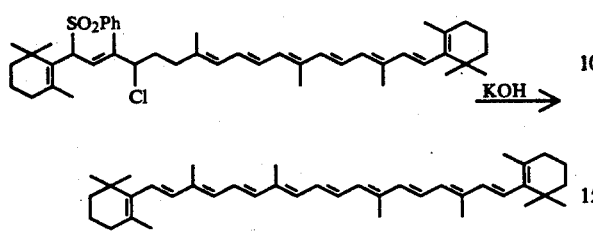

In a 50-ml round-bottom flask 1.32 g (purity: 40.9%, 0.76 mmole) of 1-phenylsulfonyl-4-chloro-1,18-di(2,6,6-trimethyl-1-cyclohexen-1-yl)-3,7,12,16-tetramethyloctadeca-2,7,9,11,13,15,17-heptaene was reacted with 0.8 g (purity: 85%, 12.1 mmoles) of potassium hydroxide in 15 g of ethanol at 45° C. for 3 hours. Then water and toluene were added and the reaction mixture was separated. The organic layer obtained was washed with water and the solvent was removed therefrom to obtain 1.95 g (purity: 17.2%, 0.62 mmole, yield: 81.6%) of β-carotene.

EXAMPLES 12 AND 13

β-carotene was obtained from the corresponding sulfone compounds in the same manner as in Example 10 or 11. The results are shown in the following table.

Synthesis Examples of β-carotene from sulfone compounds

| Example | Sulfone compound | Alkaline compound | Yield (%) of carotene |
|---------|------------------|-------------------|----------------------|
| 12 | (structure with SO₂Ph) | KOH | 61.7 |
| 13 | (structure with SO₂Ph and acetal) | MeOK | 70.0 |

Obviously, numerous modifications and variations of the present invention are possible in light of the above teachings. It is therefore to be understood that within the scope of the appended claims, the invention may be practiced otherwise than as specifically described herein.

What is claimed is:

1. A sulfone aldehyde represented by the following general formula (7), (8) or (9)

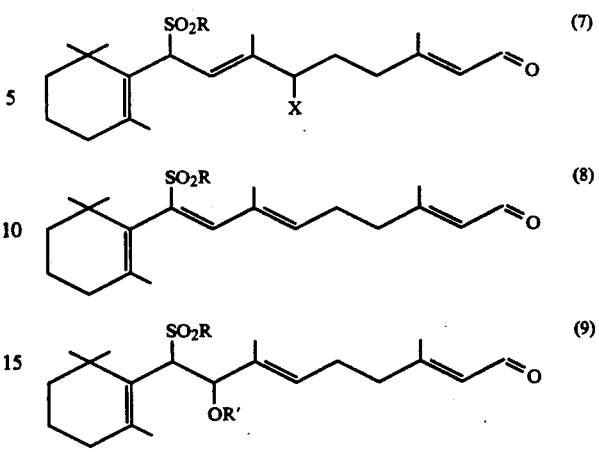

wherein R represents a phenyl group which may be substituted, R' a protecting group of acetal type and X a halogen atom.

2. The sulfone aldehyde of claim 1, represented by the formula (7).

3. The sulfone aldehyde of claim 2, wherein R represents a phenyl group or a phenyl group substituted with a lower alkyl group, a halogen or a lower alkoxy group.

4. The sulfone aldehyde of claim 3, wherein X represents chlorine, bromine or iodine.

5. The sulfone aldehyde of claim 1, represented by the formula (8).

6. The sulfone aldehyde of claim 5, wherein R represents a phenyl group or a phenyl group substituted with a lower alkyl group, a halogen or a lower alkoxy group.

7. The sulfone aldehyde of claim 6, wherein X represents chlorine, bromine or iodine.

8. The sulfone aldehyde of claim 1, represented by the formula (9).

9. The sulfone aldehyde of claim 8, wherein R represents a phenyl group or a phenyl group substituted with a lower alkyl group, a halogen or a lower alkoxy group.

10. The sulfone aldehyde of claim 9, wherein R' represents 1-ethoxyethyltetrahydrofuranyl, tetrahydropyranyl, or 4-methyltetrahydropyranyl.

* * * * *

UNITED STATES PATENT AND TRADEMARK OFFICE
CERTIFICATE OF CORRECTION

PATENT NO. : 5,237,102

DATED : August 17, 1993

INVENTOR(S) : Toshiki Mori et al

It is certified that error appears in the above-indentified patent and that said Letters Patent is hereby corrected as shown below:

Process (A) bridging columns 1 and 2, second structure,

" 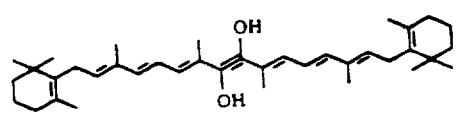 "

should read

-- 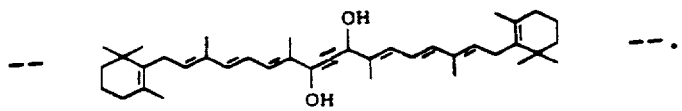 --.

Column 2, line 11, change "Na$_2$CO$_2$" to --Na$_2$CO$_3$--.

UNITED STATES PATENT AND TRADEMARK OFFICE
CERTIFICATE OF CORRECTION

PATENT NO.  : 5,237,102

DATED       : August 17, 1993

INVENTOR(S) : Toshiki Mori et al

It is certified that error appears in the above-indentified patent and that said Letters Patent is hereby corrected as shown below:

Structure bridging columns 3 and 4, lines 1-20

"

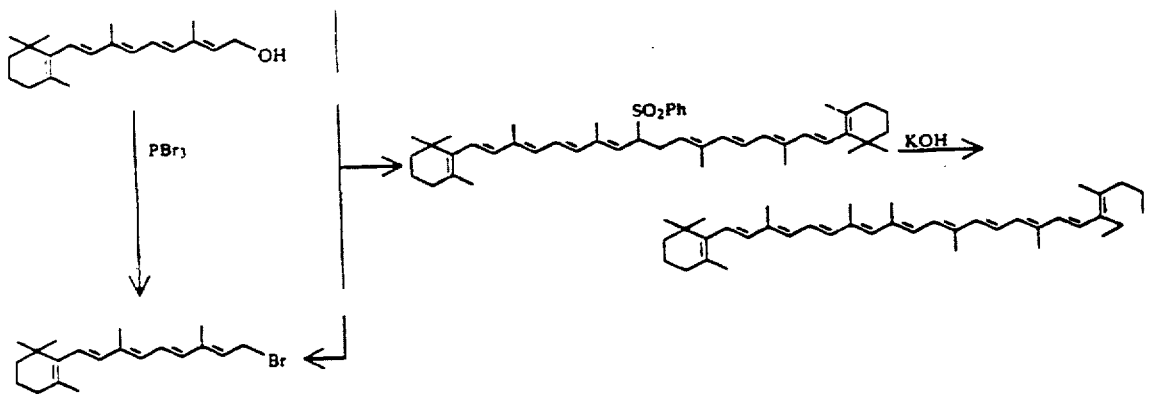

should read --

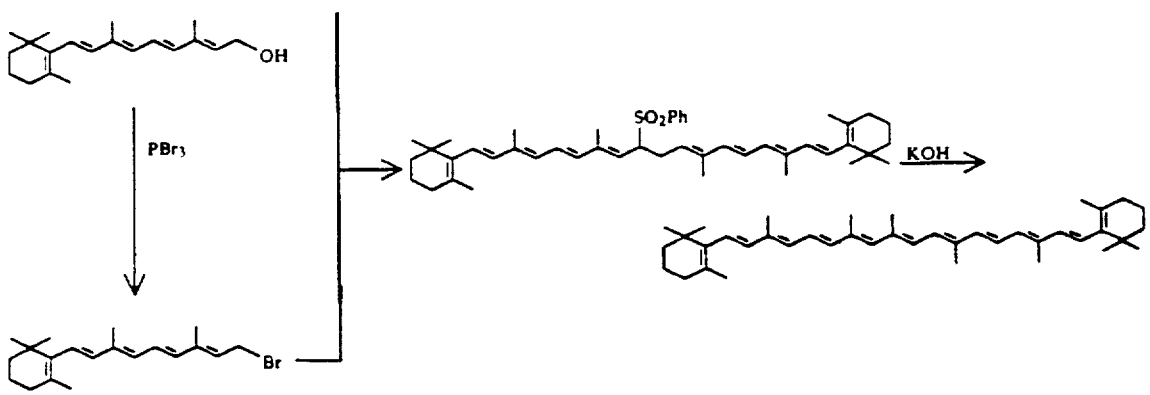

--

UNITED STATES PATENT AND TRADEMARK OFFICE
CERTIFICATE OF CORRECTION

PATENT NO. : 5,237,102
DATED : August 17, 1993
INVENTOR(S) : Toshiki Mori et al

It is certified that error appears in the above-indentified patent and that said Letters Patent is hereby corrected as shown below:

Column 3, line 60-63, formula (3)

"  "

should read -- 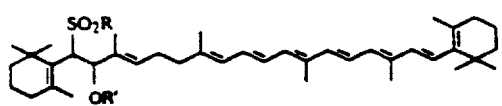 --.

Signed and Sealed this

Twenty-second Day of November, 1994

Attest:

BRUCE LEHMAN

Attesting Officer   Commissioner of Patents and Trademarks